United States Patent [19]

Wright

[11] 4,045,519

[45] Aug. 30, 1977

[54] PROCESS FOR PREPARING DIALKYLPHOSPHITES

[75] Inventor: William E. Wright, Farmington, Mich.

[73] Assignee: Ethyl Corporation, Richmond, Va.

[21] Appl. No.: 723,761

[22] Filed: Sept. 16, 1976

[51] Int. Cl.² .................... C07F 9/141; C10M 1/44
[52] U.S. Cl. ................................ 260/976; 252/32.5
[58] Field of Search .......................... 260/976, 967

[56] References Cited

U.S. PATENT DOCUMENTS 2,794,820  6/1957  Campbell .............................. 260/976

*Primary Examiner*—Anton H. Sutto
*Attorney, Agent, or Firm*—Donald L. Johnson; Robert A. Linn; Joseph D. Odenweller

[57] ABSTRACT

Dialkylphosphites are made by adding $PCl_3$ to a mixture of water and alkanol and distilling product from the resultant reaction mixture leaving a distillation residue. Alkanol is added to the residue and the mixture reacted at elevated temperature to yield additional dialkylphosphite.

5 Claims, No Drawings

PROCESS FOR PREPARING DIALKYLPHOSPHITES

BACKGROUND

Dialkylphosphite is also known as dialkyl hydrogen phosphonate. It can be made by the reaction of $PCl_3$ with alkanol evolving HCl. Water can be included in the alkanol during this reaction (Kosolapoff et al, *Organic Phosphorus Compounds*, Volume 5, Page 28).

Dialkylphosphites are useful lubricant additives. For example, di-n-butylphosphite is used in gear lubricants to provide beneficial friction and wear properties. It is referred to as an extreme pressure (EP) additive.

SUMMARY

According to the present invention, dialkylphosphites are obtained in high yield and purity by first reacting $PCl_3$ with an alkanol-water mixture and distilling off the product leaving a residue. Alkanol is then added to the residue and the mixture heated following which additional dialkylphosphite is recovered by distillation.

DESCRIPTION OF THE PREFERRED EMBODIMENTS

A preferred embodiment of this invention is a process for making a di-$C_{1-4}$ alkylphosphite in high yield, said process comprising (a) forming a mixture of about 1.8–2.5 moles of a $C_{1-4}$ alkanol and about 0.5 to 1.2 moles of water, (b) adding about one mole $PCl_3$ to said mixture and reacting at 0° to 70° C., (c) distilling dialkylphosphite from the reaction product of (b), leaving a distillation residue, (d) adding about 0.5 to 5 parts by weight of said alkanol to each part by weight of said distillation residue and heating the resultant mixture at 65° to 140° C., and (e) distilling additional dialkylphosphite from the final reaction product.

The process is operable with a wide range of alkanols in which water will dissolve. The preferred alkanols are the lower alkanols containing 1–4 carbon atoms such as methanol, ethanol, n-propanol, isopropanol, n-butanol, isobutanol, sec-butanol, and tert-butanol. Of these, the most preferred are the primary alkanols such as methanol, ethanol, n-propanol, isobutanol and n-butanol. The preferred alkanol is n-butanol.

In the first stage of the process water is mixed with the alkanol and $PCl_3$ added to it. The amount of water is preferably in the range of 0.5–1.2 moles per mole of $PCl_3$. A more preferred range is about 0.6–1.0 moles, and a most preferred amount is about 0.8 mole per mole of $PCl_3$.

The amount of alkanol used in the first stage is about 1.8–2.5 moles per mole of $PCl_3$. A preferred range is about 2–2.3 moles, and a most preferred amount is about 2.2 moles per mole of $PCl_3$.

During the reaction with $PCl_3$, HCl will be evolved. In order to facilitate its removal, the first reaction is preferably conducted at reduced pressure. A useful range is about 100–500 mm Hg.

As a further aid in removing HCl, nitrogen can be sparged through the liquid phase during the reaction to sweep out HCl.

$PCl_3$ is added to the alkanol-water mixture while cooling to hold the temperature below about 70° C. and preferably below about 20° C. Minimum reaction temperature can be quite low because the reactants are very active. Temperatures as low as −20° C. can be used. A preferred temperature range is about −10° to 20° C., and a more preferred range about −10° to 10° C.

The reaction time depends mainly on heat removal and vacuum capacity. On the laboratory scale the reaction can be completed in about 1–4 hours, but on a larger scale longer times might be required.

Following the first stage the desired dialkylphosphite is recovered by distillation. The distillation is preferably carried out at reduced pressure of about 10–250 mm Hg in order to hold temperatures down. The product is obtained in high purity having a low residual acidity.

Following the distillation a substantial amount of residue remains. This can amount to 0.05–1.0 parts by weight per part of product distilled out. In the second stage alkanol is added to this residue and the mixture is reacted at elevated temperature.

The amount of alkanol used in this second stage is not critical. A useful range is about 0.5–10 parts by weight per part of residue. A preferred range is about 0.5–5 parts, and a most preferred amount is about 0.9–1.1 parts of alkanol per part of distillation residue.

The mixture is heated to a temperature high enough to cause the formation of dialkylphosphite by reaction of the alkanol with the components of the residue. A useful temperature range is from about 65° C. up to the reflux temperature of the mixture. It is preferred to carry this stage out at reflux.

Preferably an inert water-insoluble solvent is included in the second stage. This can be used to remove water which forms by separation from an azeotrope. Preferably such solvent will have a normal boiling point in the range of about 60–180° C. Useful solvents include benzene, toluene, xylene, mesitylene, hexane, heptane, octane, nonane, chlorobenzene, dischlorobenzene and the like. The amount of solvent can vary widely. A useful range is from about 0.05 to 0.5 parts per part of reaction mixture.

The second stage reaction should be carried out for a time long enough to convert a substantial amount of the phosphorus values in the residue to dialkylphosphite. This is generally accomplished in about 1–12 hours and in most cases about 4–8 hours.

Following the second stage reaction the final reaction mixture is distilled to recover unreacted alkanol and additional dialkylphosphite. The amount of additional product obtained by this method is very substantial and can amount to about one-third of the total product produced.

The manner in which the process is conducted is illustrated by the following examples. All parts are parts by weight unless otherwise stated.

EXAMPLE 1

In a reaction vessel was placed 978.6 parts (12 moles) of n-butanol and 86.4 parts (4.8 moles) of water. To this was added 823.8 parts (6 moles) of $PCl_3$ over a 1.5 hour period at 25 to 52° C. The reaction product was then distilled to recover 860 parts of di-n-butylphosphite boiling at 122°–131° C., 15 mm Hg (74% yield).

A 193.5 part residue remained after the distillation. To this was added 193.5 parts n-butanol and 77 parts toluene. The mixture was stirred at reflux for 6 hours while removing water (23.2 parts) which azeotroped with the toluuene using a Dean Stark separator. Following this, the reaction mixture was distilled to recover 174 parts of additional di-n-butylphosphite, thus increasing the final yield from 74% to 89% of theory.

EXAMPLE 2

In a reaction vesel was placed 32.63 parts (0.44 moles) of n-butanol and 2.88 parts 0.16 moles) of water. The vessel was evacuated to 0.5 atmospheres while maintaining a nitrogen sweep through the system. Over a 1 hour 20 minute period 27.25 parts of $PCl_3$ was added at 40°–50° C. Di-n-butylphosphite was recovered from the rection mixture by distillation (130°–155° C. at 10 mm Hg), yielding 20.1 parts of product and 12.8 parts of distillation residue.

To the residue was added 12.8 parts of n-butanol and 2.6 parts of toluene. This mixture was refluxed for 6.5 hours while removing azeotrope water. The final mixture was distilled to recover 10.0 parts of additional di-n-butylphosphite giving an overall yield of 78% of theory, of which one-third was obtained in the second stage.

As shown above, the additional reaction step provides a very substantial yield increase over that obtained by the reaction of $PCl_3$ with an alkanol-water mixture. The amount of additional product can run about half again as much as obtained in the initial reaction and represents a significant economic advantage.

Other dialkylphosphites can be made following the above general procedure by substituting other alkanols for the n-butanol used in the examples. Use of methanol will yield dimethylphosphite. Likewise, ethanol will produce diethylphosphite. Likewise, ethanol will produce diethylphosphite and n-propanol will form di-n-propylphosphite. Similarly, isobutanol leads to the formation of di-isobutylphosphite.

After dialkylphosphite is distilled from the second stage reaction mixture a residue will remain which contains phosphorus values. This residue may be discarded or may be again subjected to reaction with alkanol followed by distillation to recover still further dialkylphosphite. Alternatively, all or a portion of this residue may be combined with the first stage residue of a subsequent $PCl_3$alkanol-water reaction and the combined residue subjected to reaction with alkanol and distillation.

The products made by the present process are useful in lubricating oil formulations. They are especially useful in lubricants used in gear applications such as automotive differential lugricants. In this use they function as extreme pressure (EP) additives. The following example illustrates the use of one of the products in blending a gear additive.

EXAMPLE 3

In a blending vessel place 1000 parts of an SAE 90 mineral oil, 35 parts of sulfurized nonene trimer, 5 parts di-n-butylphosphite, 5 parts oleylamine and 1 part of 2,5-bis(t-octyldithio)-1,3,4-thiadiazole. Blend the mixture until homogenous to obtain a gear lubricant for use in automotive differentials.

Dialkylphosphites are also useful as antioxidant synergists as described in U.S. Pat. No. 3,115,465.

I claim:
1. A process for making a di-$C_{1-4}$ alkylphosphite in high yield, said process comprising
   a. forming a mixture of about 1.8-2.5 moles of a $C_{1-4}$ alkanol and about 0.5 to 1.2 moles of water,
   b. adding about one mole $PCl_3$ to said mixture and reacting at about 0° to 70° C.,
   c. distilling dialkylphosphite from the reaction product of (b), leaving a distillation residue,
   d. adding about 0.5 to 5 parts by weight of said alkanol to each part by weight of said distillation residue and heating the resultant mixture at 65° to 140° C., and
   e. distilling additional dialkylphosphite from the final reaction product.
2. A process of claim 1 wherein said alkanol is a primary alkanol.
3. A process of claim 2 wherein said alkanol is a primary butanol.
4. A process of claim 3 wherein an inert water-insoluble solvent is included in step (d) and the resultant mixture of said alkanol, distillation residue and inert solvent is heated at reflux and water is separated and removed from refluxing distillate.
5. A process of claim 4 wherein said butanol is n-butanol.

* * * * *